United States Patent [19]
Schilling et al.

[11] Patent Number: 5,795,732
[45] Date of Patent: Aug. 18, 1998

[54] STIRRED-TANK REACTORS AND METHOD OF USE

[75] Inventors: Bernhard Schilling, Braunschweig; Walter Pfefferle, Halle; Bernd Bachmann, Werther; Wolfgang Leuchtenberger, Bielefeld; Wolf-Dieter Deckwer, Oldenburg, all of Germany

[73] Assignee: Degussa Aktiengesellschaft, Frankfurt, Germany

[21] Appl. No.: 657,381

[22] Filed: Jun. 3, 1996

[30] Foreign Application Priority Data

Jun. 3, 1995 [DE] Germany ............. 195 20 485.9

[51] Int. Cl.⁶ ........................... C12M 1/02; C12P 1/00
[52] U.S. Cl. ................ 435/41; 435/289.1; 422/130; 366/295; 366/307
[58] Field of Search ................. 435/286.7, 289.1, 435/299.1, 818, 4, 29, 41; 366/292, 293, 295, 302, 303, 307, 315, 316, 317; 422/130

[56] References Cited

U.S. PATENT DOCUMENTS

| | | | |
|---|---|---|---|
| 695,974 | 3/1902 | Wallerstein et al. | 435/289.1 |
| 4,906,574 | 3/1990 | Erdei et al. | 435/289.1 |

FOREIGN PATENT DOCUMENTS

| | | | |
|---|---|---|---|
| 32 45 556 | 4/1984 | Germany | 435/289.1 |
| 596615 | 3/1978 | U.S.S.R. | 435/289.1 |

*Primary Examiner*—William H. Beisner
*Attorney, Agent, or Firm*—Cushman Darby & Cushman IP Group of Pillsbury Madison & Sutro LLP

[57] ABSTRACT

The invention is relates to improved stirred-tank reactors which are suitable, due to special fittings, for converting the results of e.g. microbial or enzymatic processes obtained when they are used on a laboratory scale into an industrial scale. A shaft-driven disk agitator is provided, with at least one perforated disk being attached in the reactor above and/or below the disk agitator.

6 Claims, 1 Drawing Sheet

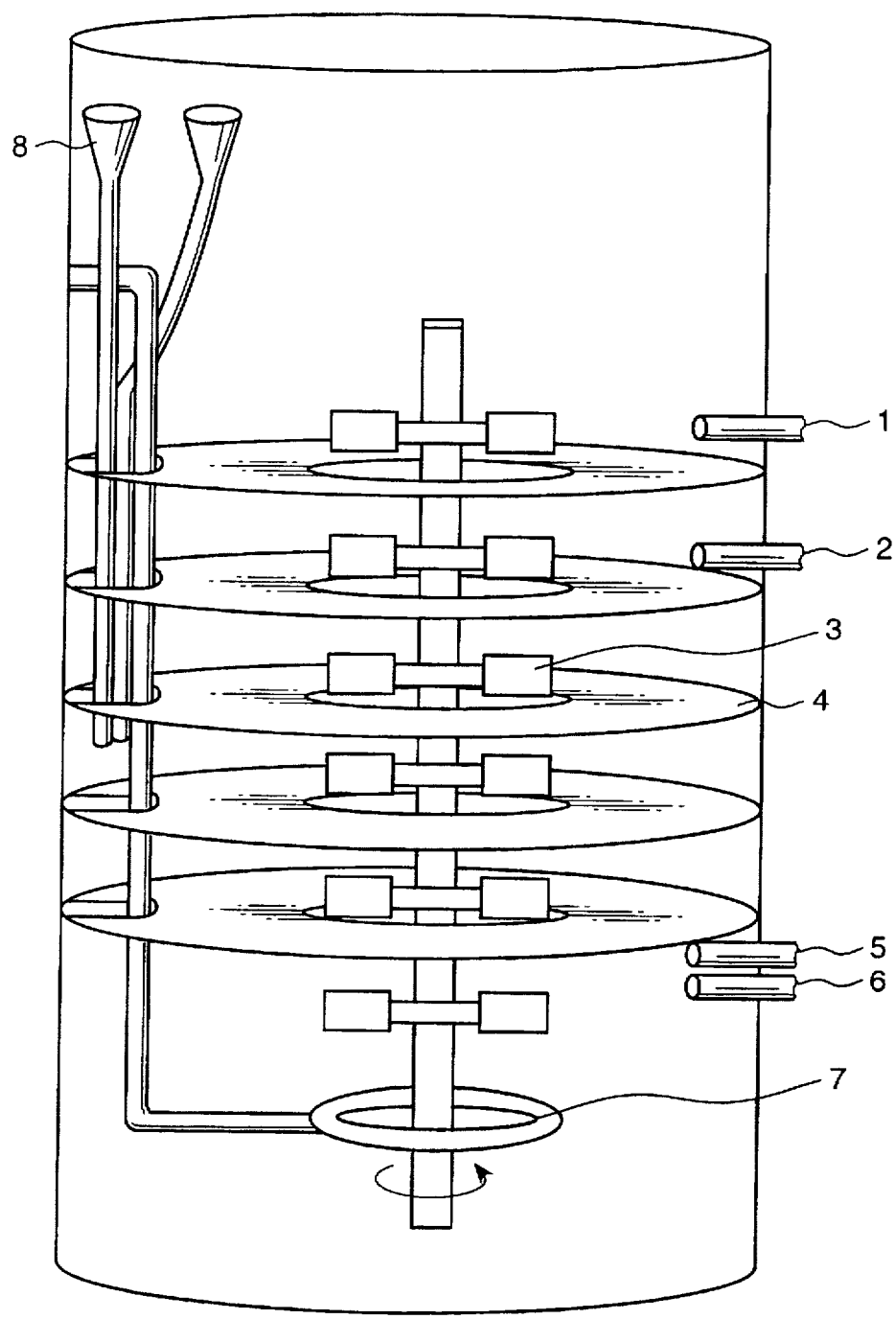

STIRRED-TANK REACTORS AND METHOD OF USE

BACKGROUND OF THE INVENTION

1. Field of the Invention

The invention relates to stirred-tank reactors intended for laboratory and test purposes which are suitable, by virtue of their special fittings, for converting the results obtained when they are used to an industrial scale.

2. The Prior Art

In general, chemical and microbial or enzymatic processes are pretested on a laboratory scale for their suitability for being converted to a commercial scale.

Microorganisms, for example, are cultured in small reactors which guarantee the most favorable prerequisites possible for growth and product formation.

Under such conditions there is a largely uniform distribution of the nutrients in the reactor with transport mechanisms between nutrient solution and microorganisms which mechanisms take place at the same time in an optimum fashion.

The charging and distribution of oxygen into the fermentation broth also constitute a significant factor in aerobic processes.

A stirred-tank reactor is very frequently used in the area of biotechnological processes on account of the possibilities of varying its design.

If the capability of a microorganism to work has shown promise on a laboratory scale, practice has shown that the transfer of this method and of its results to a production scale is associated with a number of problems. An expert in the art knows that by an order of magnitude the same working capability of a strain for the same product amount as when made on the laboratory scale cannot be expected. A reactor of such design cannot be simply enlarged in its order of magnitude by a factor X if one wishes to obtain X times the amount of product.

There are therefore many studies regarding this problem which attempt to offer starting points for a solution under certain given prerequisites.

However, the data regarding reactor design and scale conversion contained in the state of the art at times differ considerably from each other due to the different measuring processes.

Note, for example, studies of the scale-up behavior by means of mathematical models (NAGY et al., Computers Chem. Engr. Vol. 18, Suppl. 663 to 667, 1994).

On the other hand, reactor systems are described which simulate the conditions on the industrial scale by a series of stirred-tank reactors.

Thus, OOSTERHUIS et al., Biotech. Letters, Vol. 5, No. 3, 141 to 146 (1983) use two reactors connected in series in which defined, different conditions (e.g. oxygen-rich and oxygen-poor culture conditions) prevail.

The cells of the microorganisms pass in this test sequence through different, precisely defined states. However, in this manner the number of states to be measured is limited to the number of reactors. Transitional states are hardly detected and the problem of back-mixing is also neglected.

Therefore, there is still the unsolved problem of making available reactors as testing systems for the scale-up behavior of fermentation processes and enzymatic processes.

SUMMARY OF THE INVENTION

It now has been discovered that a laboratory fermenter (stirred-tank reactors), among others, can be varied by fittings as regards the relevant parameter of mixing time $ø_{90}$ in such a manner that it corresponds, given comparable volume-related efficiency charging, to a reactor of 10 to up to >100 m$^3$ which does not contain these fittings.

The invention comprises a laboratory fermenter (stirred-tank reactor) which is equipped with disk agitators, characterized in that at least one perforated disk is attached above and/or below the agitator blade or blades.

The ratio of perforated surface to disk surface is preferably 10 to 40%, especially approximately 20%. The disk surface preferably covers 60 to 90%, especially 75 to 85% of the reactor cross section.

The number of perforations can be selected at will; it is in particular between 1 and 12, and the arrangement of the perforations is advantageously as symmetric as possible.

If two or more disk agitators are mounted on the agitator shaft, generally one perforated disk is located between the agitators and preferably fastened in the middle.

However, under special conditions two equally or differently perforated disks are attached between the disk agitators, the number of which perforated disks is e.g. 2 to 10, given a height of the stirred-tank reactor of 0.75 m.

A preferred variant consists in that the perforated disks are fastened to the wall or to vertical threaded rods, of course without hindering the agitator shaft. In this manner any possible rise of gas bubbles on the reactor wall is prevented. It is also possible to fasten the perforated disks alternatingly to the agitator shaft or to the reactor wall.

It is possible, with the aid of the horizontal fittings (perforated disks) to reduce the exchange of material in vertical direction in a laboratory reactor with 10 to 500 l content to an extent which corresponds to the conditions in a reactor of 10 to >100 m$^3$ used for production. According to EINSELE et al. (Chem. Rundschau (1976), 25, 53 to 55) the mixing time $ø_{95}$ of reactors of this size is approximately 100 s.

According to this definition the term mixing time signifies that time which is necessary to obtain 95% of the final pH after the addition of a given amount of acid or lye. However, since it has been shown that the value of 95% can be determined only with difficulty, the 90% value is measured in the present application without this weakening the force of the statement of the method described by EINSELE.

This magnitude describing the mixing behavior can be readily determined in laboratory fermenters with the perforated disks built according to the invention.

A geometrically similar shape of the reactors naturally constitutes a prerequisite for a logical comparison. The volume of the reactors used for the test is within the framework of the apparatuses customarily used in the lab, that is, from 10 to 500 l, which data is not to be considered as exclusive. It is possible with the standard reactors modified in accordance with the invention to obtain a realistic picture of what influence the mixing time has, for example, on the fermentation.

The mixing time can be determined, for example, by means of the fluorescence method, pH method or conductivity method. It turns out that expressive information about substance exchanges and biomasses is obtained, using the standard reactors modified in accordance with the reactor, in a simple manner for the scale-up, e.g., of fermentation processes for which information can be sought in accordance with the state of the art only when much given data is considered and is nevertheless only obtained with a great amount of uncertainty.

The data concerning the mixing time is particularly useful when the so-called efficiency charging is given. The latter is generally around 1 to 4 kW/m³ for enzymatic reactions and fermentation processes. The no-load performance of the agitator is subtracted beforehand. Mixing times $\emptyset_{90}$ of 40 to 300 sec are to be adjusted in the stirred-tank reactors of the invention with this efficiency charging as a function of the number of fittings.

A variant of the characterization of the behavior of model reactors also consists in the indicating of the "work point" which is defined by its position in the coordinate system $\emptyset_{90}$ in comparison to the efficiency charging.

BRIEF DESCRIPTION OF THE DRAWINGS

The sole FIGURE is a schematic view of a stir-reactor according to the present invention.

DETAILED DESCRIPTION OF PREFERRED EMBODIMENTS OF THE INVENTION

EXAMPLE SECTION

Fermentation tests with strains producing L-lysine were carried out without, however, the conversion of scale being limited to the latter.

A standard reactor (40 l, ideal agitated tank) was equipped with 4 flow spoilers and 2 disk agitators with a disk diameter of 0.1 m, 0.02 m blade height mounted at ⅓ and ⅔ of the liquid level.

Six disk agitators were built into the modified standard reactor which were mounted at an interval of 7 cm on the agitator shaft. Five perforated disks were sealed off between the agitator blades from the outside against the reactor wall, mounted with a perforation diameter of 0.11 m (interval agitator perforated disk 3.5 cm). (Ratio perforated area: disk area 1:5=20%).

The sole FIGURE shows the design, in accordance with the invention, of the test reactor (perforated disks) as well as for the fittings necessary for carrying out the measuring of mixing time and fermentation.

Using the pH method (EINSELE, see supra), the mixing time $\emptyset_{90}$ was determined at 20 l filling, 400 rpm and 2 vvm aeration. 10 s for the standard reactor and 130 s for the reactor modified in accordance with the invention resulted as being mixing times, whereby corresponding test parameters can be derived therefrom for, reactors of approximately 100 m³ and more. As the following tests show, for example, clear influences on the substance conversions and the amount of the biomass formed are found.

Example 1

12 two-liter flasks were filled with 360 ml of the following agitated flask medium and sterilized 20 min at 121° C. After having cooled off the flasks were seeded with the leucine-auxotrophic lysine production strain DSM5715 and incubated 24 h at 150 rpm and 300° C. The culture broth of each 6 flasks was combined and made available as inoculum for a fermenter in each instance.

Agitated flask medium:

|  |  |  |
|---|---|---|
| Saccharose | 20 | g/kg |
| Molasses | 43.6 | g/kg |
| Soya meal hydrolysate | 120 | ml/kg |
| Yeast extract | 0.5 | g/kg |

-continued

|  |  |  |
|---|---|---|
| (NH₄)₂SO₄ | 32 | g/kg |
| Urea | 6.0 | g/kg |
| MgSO₄.7H₂O | 0.25 | g/kg |
| KH₂PO₄ | 0.5 | g/kg |
| Citric acid.H₂O | 0.6 | g/kg |
| FeSO₄.7H₂O | 10 | mg/kg |
| L-leucine | 60 | mg/kg |
| L-threonine | 40 | mg/kg |
| L-methionine | 80 | mg/kg |
| Nalco | 1 | drop/kg |
| D-biotin | 0.4 | mg/kg |
| Thiamine.HCl | 2.0 | mg/kg |
| CaCO₃ | 10 | g/kg |

The tests of examples 2 and 3 were carried out in the form of a parallel fermentation. This concept refers to the use of the same inoculum material (12 flasks are combined, the culture broth obtained is distributed in equal parts onto fermenters examples 2 and 3), the monitoring of temperature, agitator speed, pO₂ set point and feed profile for the supplementary solution.

Example 2
Fermentation in a standard reactor

The standard reactor, equipped with agitator system and tempering system, was charged with 20 l of the following medium and sterilized 30 min at 121° C.

|  |  |  |
|---|---|---|
| Saccharose | 20 | g/kg |
| Molasses | 5.3 | g/kg |
| Zein [gluten of maize] hydrolysate | 20 | ml/kg |
| (NH₄)₂SO₄ | 10 | g/kg |
| Mg sulfate.H₂O | 0.75 | g/kg |
| Citric acid.H₂O | 0.6 | g/kg |
| Fe sulfate.7H₂O | 30 | mg/kg |
| Mn sulfate.H₂O | 30 | mg/kg |
| Zn sulfate H₂O [sic] | 1.5 | mg/kg |
| CaCl₂.2H₂ | 20 | mg/kg |
| H₃PO₄ 89% | 1.75 | ml/kg |
| Biotin | 0.3 | mg/kg |
| Thiamine.HCl | 0.2 | mg/kg |
| Nalco | 1 | g/kg | with NH₄OH 25% at pH 7.5 v. before sterilization pH 7.0

After cooling off to 30° C. the fermenter is seeded with 2 liters of the inoculum. The culture is agitated at 30° C. and 400 rpm, the pO₂ value adjusted via the aeration (0.5–2 vvm) to 20% saturation. The pH is adjusted with 25% ammonia solution to pH 7. If foam accumulates Struktol is added as required to chemically combat the foam. After a drop of saccharose concentration to below 10 g/l, 2 sterile solutions are dosed in:

Feed medium sugar: 9.5 kg solution with 500 g/kg saccharose

Feed medium supplement[s]: 5 kg solution with the following composition:

|  |  |  |
|---|---|---|
| Molasses | 18 | g/kg |
| Zein hydrolysate | 50 | g/kg |
| (NH₄)₂SO₄ | 10 | g/kg |
| Mg sulfate.7H₂O | 0.375 | g/kg |
| H₃PO₄ (89%) | 0.9 | g/kg |
| Citric acid.H₂O | 0.6 | g/kg |
| Fe sulfate.7H₂O | 15 | mg/kg |
| Mn sulfate.H₂O | 15 | mg/kg |
| Zn sulfate.7H₂O | 1.5 | mg/kg |
| CaCl₂.2H₂O | 10 | mg/kg |
| Biotin | 0.3 | mg/kg |

| | | |
|---|---|---|
| Thiamine HCl | 0.2 | mg/kg |
| Nalco | 1 | mg/kg | pH 7.5 before sterilization

The sugar feeding took place in such a manner that there was always a sugar concentration >10 g/l in the reactor.

The supplementary solution was fed in continuously within 49 h.

After 53 h cultivation time the fermentation was concluded. Up to the end of cultivation 4480 g saccharose were consumed and 1021 g Lys.HCl=817 g lysine base formed. The entire dry weight of biomass was approximately 327 g.

Example 3

Fermentation in the modified standard reactor

The reactor was filled with the same medium as described in example 2 and sterilized. After adjustment of the fermentation parameters as in example 2 the fermenter was seeded with 2 liters of the inoculum material according to example 1. The conducting of the fermentation (temperature, speed, $pO_2$ set point, feed profile for supplementary solution) corresponds to that of the standard reactor operated in parallel. After 53 h cultivation time the fermentation was concluded. Up to this point in time 3852 g saccharose were consumed and 902 g Lys.HCl or 722 g lysine base formed. The entire dry mass was approximately 305 g.

The parallel fermentations show that the substance conversions were reduced very clearly (by about 14%), the dry weight of biomass noticeably (by about 7%) by means of the fillings in the test reactor, which lead to a mixing time customary in large reactors. This information is significant for the scale-up of a production process.

Thus, the behavior of a fermentation process in large reactors can be simulated very efficiently and economically by means of the selected equipment of the test reactor. It is possible therewith to eliminate the cost-intensive adaptation of the process in fermenters of increasing size and to immediately adapt the processing to the conditions at a mixing time of $\emptyset_{90}$ of approximately 130 s, as is found for reactors of approximately 100 m³ and more volume.

A picture of the test reactor which is preferably used is shown in the sole FIGURE.

The numbers in the figure have the following significance:

1. Upper pH electrode
2. Upper $pO_2$ electrode
3. Disk agitator (total of six agitators)
4. Perforated disk (total of five perforated disks)
5. Lower pH electrode
6. Lower $pO_2$ electrode
7. Gassing ring
8. Feeding tube

What is claimed is:

1. A fermenting device for pretesting microbial and enzymatic processes in simulated production scale conditions comprising:

a stirred-tank reactor having a volume of 10 to 500 l and equipped with at least one shaft driven disk agitator; and at least one perforated disk attached within the housing in a substantially horizontal plane above and/or below the disk agitator, the ratio of the perforation area of the disk to the entire disk area being 10% to 40%.

2. A fermenting device according to claim 1 having up to 10 disk agitators and up to 11 perforated disks.

3. A fermenting device according to claims 1 or 2 having a mixing time $\emptyset_{90}$ of 40 to 300 sec at an efficiency charging of 1 to 4 kW/m³.

4. A method for simulating production scale conditions when pretesting microbial and enzymatic processes, comprising:

introducing matter to be pretested into a stirred-tank reactor having:

(a) a volume of 10 to 500 l;

(b) at least one shaft driven disk agitator; and (c) at least one perforated disk attached within the housing in a substantially horizontal plane above and/or below the disk agitator, the ratio of the perforation area of the disk to the entire disk area being 10% to 40%; and fermenting the matter in said reactor.

5. A method according to claim 4, wherein the reactor has up to 10 disk agitators and up to 11 perforated disks.

6. A method according to claims 4 or 5, wherein during fermentation the matter is mixed by said agitators with a mixing time $\emptyset_{90}$ of 40 to 300 sec at an efficiency charging of 1 to 4 KW/m³.

* * * * *